US010119210B1

(12) United States Patent
Lai et al.

(10) Patent No.: US 10,119,210 B1
(45) Date of Patent: Nov. 6, 2018

(54) TEXTILE MACHINE ADJUSTMENT METHOD AND SYSTEM THEREOF

(71) Applicant: INSTITUTE FOR INFORMATION INDUSTRY, Taipei (TW)

(72) Inventors: Ying-Hsun Lai, Tainan (TW);
Chin-Feng Lai, Kaohsiung (TW);
Yao-Chung Chang, Taitung (TW);
Yu-Cheng Hsiao, Taipei (TW);
Chi-Cheng Chuang, Kaohsiung (TW)

(73) Assignee: INSTITUTE FOR INFORMATION INDUSTRY, Taipei (TW)

( * ) Notice: Subject to any disclaimer, the term of this patent is extended or adjusted under 35 U.S.C. 154(b) by 0 days.

(21) Appl. No.: 15/834,327

(22) Filed: Dec. 7, 2017

(30) Foreign Application Priority Data

Nov. 22, 2017 (TW) .............................. 106140581 A

(51) Int. Cl.
*G06F 19/00* (2018.01)
*D04B 15/99* (2006.01)
*D04B 15/96* (2006.01)
*G01N 21/86* (2006.01)

(52) U.S. Cl.
CPC ............. *D04B 15/99* (2013.01); *D04B 15/96* (2013.01); *G01N 21/86* (2013.01)

(58) Field of Classification Search
CPC .... D04B 15/96; D04B 15/99; G01N 21/8444; G01N 21/86; G01N 21/89; G01N 21/8914; G01N 21/898; G01N 21/8983; G01N 2021/8609

USPC ................ 700/130, 134, 136, 140, 143, 144
See application file for complete search history.

(56) References Cited

U.S. PATENT DOCUMENTS

| | | | |
|---|---|---|---|
| 4,758,968 A * | 7/1988 | Lord .................... | D01G 31/006 700/144 |
| 5,873,392 A * | 2/1999 | Meyer ...................... | D03J 1/00 700/143 |
| 6,100,989 A * | 8/2000 | Leuenberger ....... | G01N 21/8983 250/208.1 |
| 6,950,717 B1 * | 9/2005 | Pierce .................... | D06C 21/00 700/136 |
| 6,987,867 B1 | 1/2006 | Meier et al. | |
| 7,187,995 B2 * | 3/2007 | Floeder .................. | G01N 21/89 700/143 |
| 2004/0133297 A1 | 7/2004 | Vergote et al. | |

(Continued)

*Primary Examiner* — Nathan Durham
(74) *Attorney, Agent, or Firm* — Birch, Stewart, Kolasch & Birch, LLP

(57) ABSTRACT

A textile machine adjustment method is provided. An operating speed of a textile machine within an operating range is set by a processor according to the basic information of the fabric. A motion image of the fabric and the vibration characteristics of the yarns are recorded by a video camera. The operating speed of the textile machine is adjusted at least once, and the vibration characteristics of the yarns is analyzed after each adjustment of the operating speed. Multiple correlation factor functions and the relative weights of the multiple factors related to the operating speed of the textile machine are recorded. The relative weights of the multiple factors are adjusted according to a yield quality of the fabric. When an expected value is met, the fabric continues to be produced at the current operating speed; otherwise, the relative weights of multiple factors are adjusted to correct the operating speed.

14 Claims, 3 Drawing Sheets

(56) References Cited

U.S. PATENT DOCUMENTS

| | | | | |
|---|---|---|---|---|
| 2005/0016428 A1* | 1/2005 | Koerner | ............... | D05B 19/14 |
| | | | | 112/117 |
| 2010/0157301 A1* | 6/2010 | Miyahara | ........... | B65H 63/0324 |
| | | | | 356/431 |
| 2012/0310404 A1* | 12/2012 | Schmidt | ................ | B65H 63/06 |
| | | | | 700/143 |
| 2016/0177481 A1* | 6/2016 | Wolf | ..................... | D03D 49/62 |
| | | | | 700/140 |

* cited by examiner

TEXTILE MACHINE ADJUSTMENT METHOD AND SYSTEM THEREOF

This application claims the benefit of Taiwan application Serial No. 106140581, filed Nov. 22, 2017, the subject matter of which is incorporated herein by reference.

BACKGROUND OF THE INVENTION

Field of the Invention

The invention relates in general to a textile machine, and more particularly to a textile machine adjustment method and a system thereof.

Description of the Related Art

As the variety and specification of the fabric are getting more diversified, quite often the textile industry needs to undertake orders with small volume and diversified specifications. Since the textile machine still has not developed fixed operating parameters for new fabrics, the operators normally need to spend a large amount of time performing adjustment and trials. If the operating speed of the textile machine is too fast or the tension is too strong, the yarns may easily break. Additionally, the operating parameters at each manufacturing stage of the textile machine are firstly set by experienced operators, and then are adjusted according to actual manufacturing process. Since the state of the machines and mechanical components will change along with their operating hours and the adjustment or correction takes time, problems of the yield quality may being unstable and the adjustment or correction time being too long will occur.

SUMMARY OF THE INVENTION

The invention is directed to a textile machine adjustment method and system thereof capable of quickly finding an optimum operating speed to reduce the textile machine adjustment time and increase quality stability of the fabric.

According to one embodiment of the invention, a textile machine adjustment method is provided. The textile machine adjustment method includes the following steps performed by a processor. A basic information of a fabric is inputted to the processor, and an operating speed of a textile machine within an operating range is set by the processor according to the basic information of the fabric. A motion image of the fabric at the current operating speed, and the vibration characteristics of multiple yarns of the fabric are recorded by a video camera. The operating speed of the textile machine is adjusted at least once by the processor, and the vibration characteristics of the multiple yarns is analyzed after each adjustment of the operating speed. Multiple correlation factor functions related to the operating speed of the textile machine are recorded, wherein the multiple correlation factor functions includes multiple factors each having a relative weight and being constructed according to the basic information of the fabric and the vibration characteristics of the multiple yarns. The relative weights of multiple factors are adjusted according to a yield quality of the fabric, wherein the processor enables the textile machine to continue to produce the fabric at the current operating speed when the yield quality of the fabric meets an expected value or the processor adjusts the relative weights of multiple factors to correct the operating speed when the yield quality of the fabric does not meet the expected value.

According to another embodiment of the invention, a textile machine adjustment system is provided. The textile machine adjustment system includes a connection interface, a video camera, a storage device and a processor. The connection interface is connected to a textile machine for receiving a basic information of a fabric and an operating speed of the textile machine. The video camera is disposed in front of the textile machine for recording a motion image of the fabric at the current operating speed and the vibration characteristics of a plurality of yarns of the fabric. The storage device is used for storing the basic information of the fabric, the operating speed of the textile machine, and the motion image of the fabric at the current operating speed. The processor is electrically connected to the video camera and the storage device via the connection interface, wherein the processor sets the operating speed of the textile machine within an operating range according to the basic information of the fabric, adjusts the operating speed of the textile machine at least once, and analyzes the vibration characteristics of the multiple yarns after each adjustment of the operating speed. The processor records a plurality of correlation factor functions related to the operating speed of the textile machine, wherein the correlation factor functions include a plurality of factors each having a relative weight and being constructed according to the basic information of the fabric and the vibration characteristics of the yarns. The processor adjusts the relative weights of the factors according to a yield quality of the fabric. The processor enables the textile machine to continue to produce the fabric at the current operating speed when the yield quality of the fabric meets an expected value or the processor adjusts the relative weights of the factors to correct the operating speed when the yield quality of the fabric does not meet the expected value.

The above and other aspects of the invention will become better understood with regard to the following detailed description of the preferred but non-limiting embodiment(s). The following description is made with reference to the accompanying drawings.

DETAILED DESCRIPTION OF THE INVENTION

Figure 1:
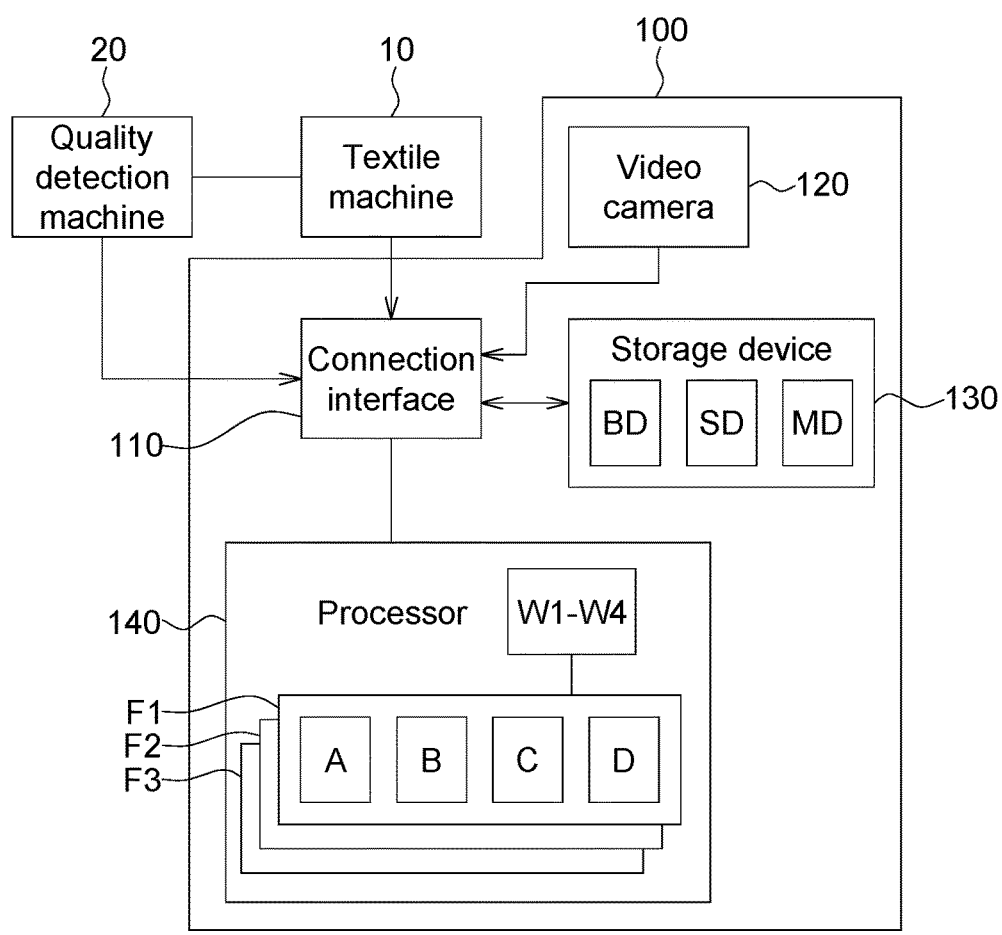
FIG. 1 is a schematic diagram of a textile machine adjustment system according to an embodiment of the invention.
Figure 2:
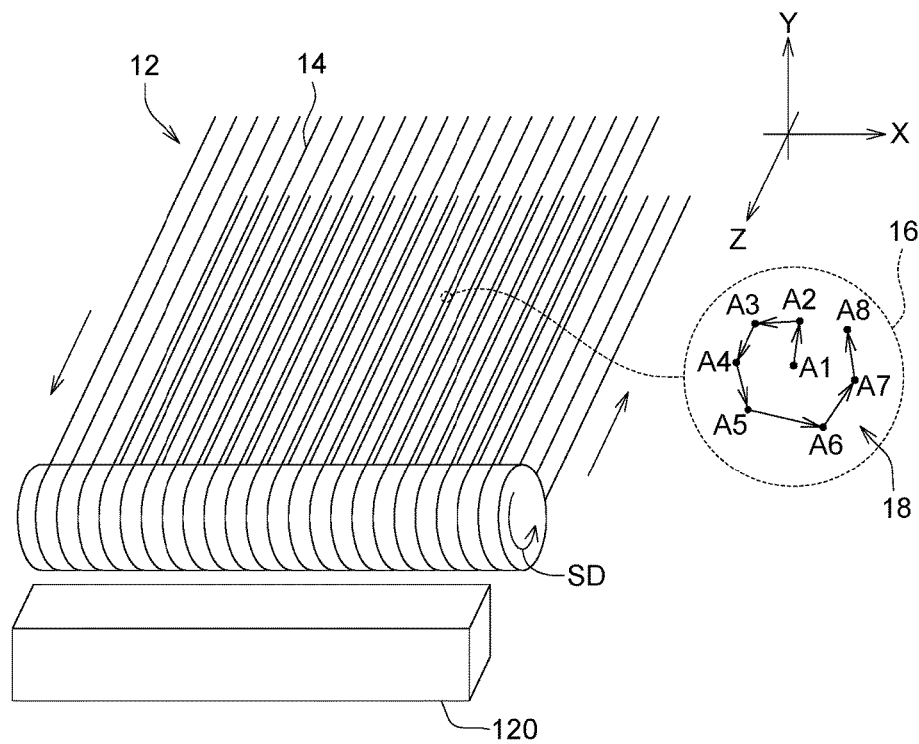
FIG. 2 is a front view of yarns and an enlarged view of a motion locus of position points of a yarn.
Figure 3:
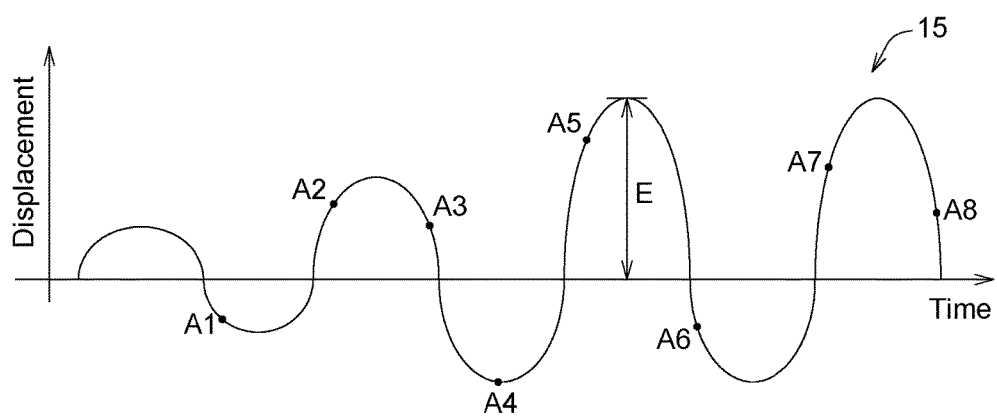
FIG. 3 is a schematic diagram of a vibration curve of position points of a yarn on the Y axis.

FIG. 1 is a schematic diagram of a textile machine adjustment system 100 according to an embodiment of the invention. FIG. 2 is a front view of the yarns 14 and an enlarged view of a motion locus 18 of position points of a yarn 14. FIG. 3 is a schematic diagram of a vibration curve of position points A1-A8 of a yarn 14 on the Y axis.

According to an embodiment of the invention, the textile machine adjustment system 100 performs quality control according to the variety and fiber specification of the fabric 12 and finds out the factors affecting the yield quality to assure that the yield quality of the fabric 12 meets an expected value.

According to an embodiment of the invention, the adjustment system 100 adjusts the operating speed SD of the textile machine 10 according to the yield quality of the fabric 12 on the production line and finds out the relative weights of the correlation factors related to the operating speed SD of the textile machine 10. When the yield quality of the fabric 12 does not meet the expected value, the adjustment system 100 adjusts the relative weight of the correlation factor to correct the operating speed SD of the textile machine 10. When the yield quality of the fabric 12 meets the expected value, the adjustment system 100 enables the textile machine 10 to continue to produce the fabric 12 at the current operating speed SD.

According to an embodiment of the invention, the correlation factors related to the operating speed SD of the textile machine 10 are such as the material of the fabric 12, the Danny number of the fabric 12, the fiber specification of the fabric 12, the twist of the fabric 12, and the processing method of the fabric 12 or a combination of the above factors. The adjustment system 100 uses above factors as a basic information BD for setting an initial operating speed of the textile machine 10 to initially set the operating speed SD of the textile machine 10 within an operating range.

According to an embodiment of the invention, the correlation factors related to the operating speed SD of the textile machine 10 are such as the vibration state or amplitude of each yarn 14 of the fabric 12, the vibration cycle T or frequency of each yarn 14, and the maximum displacement E of each yarn 14 or a combination of the above factors. The adjustment system 100 adjusts the operating speed SD of the textile machine 10 to optimally adjust the operating speed SD according to the relative weights of above factors.

According to an embodiment of the invention, the adjustment system 100 includes a video camera 120 disposed in front of the textile machine 10 for recording a motion image MD of the fabric 12 and recording the vibration characteristics of each yarn 14 of the fabric 12. Based on the image, the adjustment system 100 analyzes the vibration characteristics of each yarn 14 of the fabric 12 to adjust the operating speed SD of the textile machine 10 and record the adjusted operating speed SD and the correlation factor functions F1-F3. Then, the quality detection machine 20 determines whether one of the factors of the correlation factor functions F1-F3 affects the yield quality of the fabric 12.

According to an embodiment of the invention, the processor 140 increases the relative weight of the positive correlation factor when one of the factors affecting the yield quality of the fabric 12 is determined as a positive correlation factor, but reduces the relative weight of the negative correlation factor when one of the factors affecting the yield quality of the fabric 12 is determined as a negative correlation factor.

Detailed descriptions of the invention are disclosed below with a number of embodiments. However, the disclosed embodiments are for explanatory and exemplary purposes only, not for limiting the scope of protection of the invention. Similar/identical designations are used to indicate similar/identical elements. It should be noted that following embodiments are explained using a computer or processor 140. The textile machine adjustment method is not limited to be performed by hardware such as a computer or the processor 140. Instead, the textile machine adjustment method can also be realized by a computer program or an algorithm stored in the computer for executing the same function or procedure, and the invention is not limited thereto.

Refer to FIG. 1. The textile machine adjustment system 100 according to an embodiment of the invention includes a connection interface 110, a video camera 120, a storage device 130 and a processor 140. The connection interface 110 can be connected to one or more than one textile machine 10, such as an input/output interface or a network communication interface, for receiving and storing a basic information BD of a fabric 12 and an operating speed SD of the textile machine 10 in the storage device 130. In an embodiment, the initial operating speed of the textile machine 10 can be set according to the basic information BD of the fabric 12 or historical manufacturing data of the fabric 12.

For example, the basic information BD of the fabric 12 includes at least one of the material of the fabric 12, the Danny number of the fabric 12, the fiber specification of the fabric 12, the twist of the fabric 12, and the processing method of the fabric 12. The material of the fabric 12 can be polyester, nylon polyamine, acrylic, polypropylene, cotton, hemp, wool or yarn. The yarns 14 of the fabric 12 can be original yarns, false twisting textured yarn, textured yarns air-entangled and interlaced in the false twisting process, or textured yarns air-entangled and heat-set using a heating box. The processing method of the fabric 12 includes performing a false twisting process, such as an extension process, a false twisting process or a heat-setting process, to change the cross section and shape of the yarns 14 such that the yarns 14 can have properties such as slimness, expansion, softness, shininess, cool or hanging. Examples of most commonly seen yarns include woolenex yarns, whitelea yarns, jolie yarns, two tone yarns, fancy yarns, different shrinkage yarns and crimp yarns.

When the fabric 12 is a new variety or is formed of different materials or has different specifications of the yarns, a long time is required for adjusting the parameters of the textile machine 10. Furthermore, since the operators normally need to perform several adjustments for adjusting the operating parameters to the required values at each manufacturing stage of the textile machine 10, the production efficiency of the textile machine 10 is affected. Based on the image, the adjustment system 100 analyzes the vibration characteristics of each yarn 14 of the fabric 12 to adjust the operating parameter of the textile machine 10 and quickly obtain the optimum operating speed SD, and therefore resolves the problem encountered in the traditional method that parameters take a long time to adjust.

Refer to FIG. 1 and FIG. 2. The video camera 120 is disposed right in front of the textile machine 10 in a direction parallel to the moving direction of the fabric 12 (the Z-axis direction). The video camera 120 is used for capturing the front image of each yarn 14 of the fabric 12 and recording a motion image MD of each yarn 14 on an orthographic projection plane 16. The height of the video camera 120 is basically aligned with an initial height of each yarn 14 and is used as a view point for observing the vibration of each yarn 14. The orthographic projection plane 16 refers to a plane perpendicular to the moving direction of each yarn 14. The position points A1-A8 of each yarn 14 can form a motion locus 18 on the orthographic projection plane 16 as indicated in the enlarged view (FIG. 2). The enlarged view only illustrates the motion locus 18 of one of the yarns 14.

Refer to FIG. 1. The storage device 130 is used for storing the basic information BD of the fabric 12, the operating speed SD of the textile machine 10, and the motion image MD (that is, the motion locus 18) of the fabric 12 at the operating speed SD. The processor 140 is electrically connected to the video camera 120 and the storage device 130 via the connection interface 110 for capturing the basic information BD of the storage device 130 or the initial operating speed, and recording new result of analysis data or the adjusted operating speed SD in the storage device 130.

When the processor 140 obtains the basic information BD of the fabric 12, the processor 140 sets the operating speed SD of the textile machine 10 within an operating range according to the basic information BD of the fabric 12 and the video camera 120 is used to record the motion image MD of the fabric 12 and the vibration characteristics of each yarn 14 of the fabric 12. In an embodiment, the initial operating speed of the textile machine 10 is such as 120 rpm, and the operating range is set to be within a range of 100-150 rpm. Then, the processor 140 exemplarily adjusts the operating speed SD of the textile machine 10 to 100 or 150 rpm, and again uses the video camera 120 to record the motion image MD of the fabric 12 and the vibration characteristics of each yarn 14 of the fabric 12. The above steps are repeated at least once, and the processor 140 analyses the vibration characteristics of each yarn 14 of the fabric 12 after each adjustment of the operating speed SD.

Refer to FIG. 2. Based on the above analysis of image, the motion locus 18 of a yarn 14 on the orthographic projection plane 16 can be represented by position points A1-A8 representing the projection positions of the yarn 14 on the orthographic projection plane 16 at different time points. A motion locus 18 can be formed by connecting the position points A1-A8 observed at different time points. The motion locus 18 can be irregular or non-periodic. In an embodiment, the displacement of each of the position points A1-A8 with respect to an view point of the video camera 120 is represented by A; the angular displacement of each of the position points A1-A8 with respect to the Y axis of the view point is represented by θ; the displacement of each of the position points A1-A8 on the Y axis can is according to A and θ and expressed as A cos θ, wherein A cos θ can be the vertical displacement each of the position points A1-A8 with respect to an view point, that is, the amplitude of each of the position points A1-A8 on the motion locus 18. Besides, the time required for the position points A1-A8 to make one circuit of the view point is used as a period of the motion locus 18, and the vibration characteristics of each yarn 14 of the fabric 12 is calculated according to the amplitude and the period of the motion locus 18.

According to the above analysis of image, after the displacement and angular displacement of each of the position points A1-A8 on the motion locus 18 are calculated, the displacements and angular displacements corresponding to the position points A1-A8 can be converted to time-domain signals through regression transformation to obtain the vibration curve 15 of FIG. 3, and the vibration characteristics of each yarn 14 of the fabric 12 can be calculated according to the amplitude of and the period of the vibration curve 15.

Besides, the processor 140 further records a motion path of each yarn 14 on the Y axis of the orthographic projection plane 16. The motion path is the projection of the position points A1-A8 on the Y axis. When each yarn 14 is in a still state, each yarn 14 has an initial height. When the textile machine 10 starts to operate, the height of each yarn 14 on the Y axis has a maximum displacement E (also referred as the absolute displacement) with respect to the initial height. The textile machine adjustment system 100 records and analyzes the sum of maximum displacement E of all yarns 14 and calculates the vibration characteristics of each yarn 14 of the fabric 12 according to the sum of maximum displacement E of all yarns 14.

As disclosed above, in the present embodiment, the processor 140 can analyze the motion locus 18 and vibration characteristics (such as the amplitude, the period and the maximum displacement E) of each yarn 14 on the orthographic projection plane 16 to find out factors related to the operating speed SD of the textile machine 10 and accordingly adjust the operating speed SD of the textile machine 10. Refer to FIG. 3. The processor 140 can use an algorithm to calculate and record a plurality of correlation factor functions F1-F3 related to the operating speed SD of the textile machine 10. The correlation factor functions F1-F3 include a plurality of factors A-D respectively having one of the relative weights W1-W4. For example, the relative weight of factor A is W1; the relative weight of factor B is W2; the relative weight of factor C is W3; the relative weight of factor D is W4. Furthermore, relative weights can be assigned to a quadratic form or a cubic form of factor A, such as $A^2$ or $A^3$. Also, relative weights can be assigned to the crosslinking factors of different factors, such as crosslinking factor AB of factors A and B or crosslinking factor AC of factors A and C.

In the present embodiment, factors of the correlation factor functions F1-F3 related to the operating speed SD of the textile machine 10 include the material of the fabric 12, the Danny number of the fabric 12, the fiber specification of the fabric 12, the twist of the fabric 12 and the processing methods of the fabric 12. The relative weight of each factor can be a definite value or an indefinite value.

Besides, factors of the correlation factor functions F1-F3 related to the operating speed SD of the textile machine 10 include the motion locus 18 and the vibration characteristics (such as the amplitude, the period and the maximum displacement E) of each yarn 14 on the orthographic projection plane 16. The relative weight of each vibration factor can be a variable value. In the present embodiment, the relative weights of the factors can be obtained by resolving simultaneous correlation factor functions F1-F3. For example, the relative weights of the three factors (the amplitude, the period and the maximum displacement E) can be obtained by resolving the three simultaneous correlation factor functions F1-F3.

Refer to FIG. 1. Based on the yield quality of the fabric 12 detected by the quality detection machine 20 every time when the operating speed SD is adjusted, the processor 140 determines which factor is a positive correlation factor affecting the yield quality of the fabric 12 and which factor is a negative correlation factor affecting the yield quality of the fabric 12, and constructs the relationship between the yield quality and the operating speed according to the positive and negative correlation factors. Through the analysis of multivariate linear regression, the processor 140 adjusts the relative weight of the factor of the correlation factor functions F1-F3 that is determined as a positive correlation factor or a negative correlation factor to adjust the operating speed SD of the textile machine 10, so that the operating speed can be optimally adjusted.

For example, during the trial operation of the textile machine 10, the operating speed SD of the textile machine 10 is such as 100, 120, or 150 rpm. After the processor 140 adjusts the relative weights of the factors A-D of the correlation factor functions F1-F3 affecting the yield quality of the fabric 12, the operating speed SD of the textile machine 10 is correspondingly adjusted to 135 rpm. Then, the textile machine 10 operates at 135 rpm, and the quality detection machine 20 detects whether the yield quality of the fabric 12 meets an expected value. When the yield quality of the fabric 12 meets the expected value, the textile machine 10 continues to operate at the operating speed SD of 135 rpm to produce the fabric 12. When the yield quality of the fabric 12 does not meet the expected value, the processor 140 again adjusts the relative weights of the correlation factors to correct the operating speed SD, and again detects the yield quality.

In an embodiment, the detection of the yield quality of the fabric 12 includes detecting the quantity and the density of defects of the yarns 14. For example, the quantity of defects within a unit length or within a unit area of the fabric cannot be over a predetermined value. Apart from that, the determination of the yield quality can also be based on the size, shape, distribution or differentiation of defects.

Figure 4:
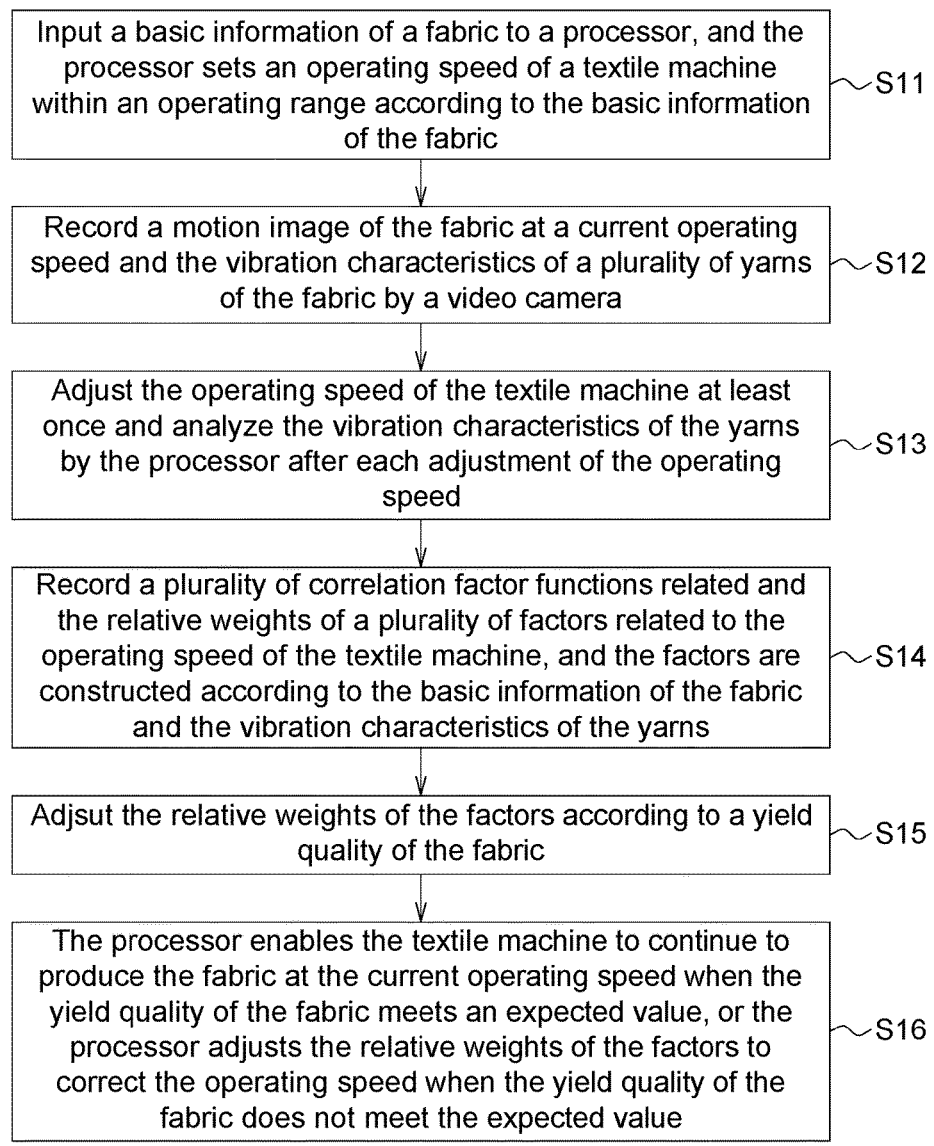
FIG. 4 is a flowchart of a textile machine adjustment method according to an embodiment of the invention.

According to the above disclosure, the invention provides a textile machine adjustment method 101 including the following steps performed by the processor 140. Refer to FIG. 4. Firstly, the method begins at step S11, a basic information BD of a fabric 12 is inputted to a processor 140, and the processor 140 sets an operating speed SD of a textile machine 10 within an operating range according to the basic information BD of the fabric 12. Then, in step S12, a motion image MD of the fabric 12 at a current operating speed SD and the vibration characteristics of a plurality of yarns 14 of the fabric 12 are recorded by a video camera 120. Then, in step S13, the operating speed SD of the textile machine 10 is adjusted at least once by the processor 140, and the vibration characteristics of the yarns 14 is analyzed after each adjustment of the operating speed SD. Then, in step S14, a plurality of correlation factor functions and the relative weights of a plurality of factors related to the operating speed SD of the textile machine 10 are recorded, and the factors are constructed according to the basic information BD of the fabric 12 and the vibration characteristics of each yarn 14 of the fabric 12. Then, in step S15, the relative weights of the factors are correspondingly adjusted according to a yield quality of the fabric 12. Then, in step S16, the processor 140 enables the textile machine 10 to continue to produce the fabric 12 at the current operating speed SD when the yield quality of the fabric 12 meets an expected value, while the processor 140 adjusts the relative weights of multiple factors to correct the operating speed SD when the yield quality of the fabric 12 does not meet the expected value.

A textile machine adjustment method and a system thereof are disclosed in above embodiments of the invention. Based on the vibration image, the adjustment system of the invention analyzes the vibration characteristics of each yarn of the fabric to adjust the operating speed of the textile machine and record the adjusted operating speed and each factor of the correlation factor functions. Then, the processor determines whether one factor of the correlation factor functions affects the yield quality of the fabric 12 by the quality detection machine. In comparison to the traditional method in which operating parameters need to be adjusted by experienced operators, the invention can quickly find out an optimal operating speed to reduce the adjustment time of the machine.

While the invention has been described by way of example and in terms of the preferred embodiment(s), it is to be understood that the invention is not limited thereto. On the contrary, it is intended to cover various modification and similar arrangements and procedures, and the scope of the appended claims therefore should be accorded the broadest interpretation so as to encompass all such modification and similar arrangements and procedures.

What is claimed is:

1. A textile machine adjustment method comprising following steps performed by a processor, wherein the method comprises:

inputting a basic information of a fabric to the processor, wherein the processor sets an operating speed of a textile machine within an operating range according to the basic information of the fabric;

recording a motion image of the fabric at a current operating speed and vibration characteristics of a plurality of yarns of the fabric by a video camera;

adjusting the operating speed of the textile machine at least once and analyzing the vibration characteristics of the yarns by the processor after each adjustment of the operating speed;

recording a plurality of correlation factor functions related to the operating speed of the textile machine, wherein the correlation factor functions comprise a plurality of factors each having a relative weight and being constructed according to the basic information of the fabric and the vibration characteristics of the yarns; and adjusting the relative weights of the factors according to a yield quality of the fabric, wherein the processor enables the textile machine to continue to produce the fabric at the current operating speed when the yield quality of the fabric meets an expected value, or the processor adjusts the relative weights of the factors to correct the operating speed when the yield quality of the fabric does not meet the expected value.

2. The adjustment method according to claim 1, wherein the basic information of the fabric comprises at least one of a material, Danny number, fiber specification, twist, and a processing method of the fabric.

3. The adjustment method according to claim 1, wherein the step of recording and analyzing the vibration characteristics of the yarns comprises recording a motion locus of each yarn in the motion image on a projection plane perpendicular to a moving direction of the yarns, wherein the motion locus of each yarn has a plurality of position points, and the processor analyzes and uses a displacement of the position points with respect to an view point as an amplitude of the motion locus, uses a time required for the position points to make one circuit of the observation point as a period of the motion locus, and constructs the factors according to the amplitude and the period of the motion locus.

4. The adjustment method according to claim 3, wherein the step of recording and analyzing the vibration characteristics of the yarns further comprises recording a motion path of the motion locus of each yarn on an axial direction of the projection plane, wherein the motion path is a projection of the position points on the axial direction, each yarn has an initial height, and the processor analyzes a maximum displacement of each height of the position points on the axial direction with respect to the initial height, and constructs the factors according to the maximum displacement.

5. The adjustment method according to claim 4, wherein the video camera is disposed in a direction parallel to the moving direction of the yarns, and a height of the video camera is aligned with the initial height of the yarns.

6. The adjustment method according to claim 1, wherein the step of adjusting the relative weights of a plurality of factors comprises determining whether one of the factors affecting the yield quality of the fabric is a positive correlation factor or a negative correlation factor, wherein the processor increases the relative weight of the positive correlation factor when the one factor is determined as a positive correlation factor or reduces the relative weight of the negative correlation factor when the one factor is determined as a negative correlation factor.

7. The adjustment method according to claim 1, wherein the step of detecting the yield quality of the fabric comprises detecting quantity and density of defects of the yarns.

8. An textile machine adjustment system, comprising:
a connection interface connected to a textile machine for receiving a basic information of a fabric and an operating speed of the textile machine;
a video camera disposed in front of the textile machine for recording a motion image of the fabric at a current operating speed and vibration characteristics of a plurality of yarns of the fabric;
a storage device used for storing the basic information of the fabric, the operating speed of the textile machine, and the motion image of the fabric at the operating speed; and
a processor electrically connected to the video camera and the storage device via a connection interface, wherein the processor sets the operating speed of the textile machine within an operating range according to the basic information of the fabric, adjusts the operating speed of the textile machine at least once, and analyzes the vibration characteristics of the yarns after each adjustment of the operating speed,
wherein the processor records a plurality of correlation factor functions related to the operating speed of the textile machine, the correlation factor functions comprise a plurality of factors each having a relative weight and being constructed according to the basic information of the fabric and the vibration characteristics of the yarns;
wherein the processor adjusts the relative weights of the factors according to a yield quality of the fabric; the processor enables the textile machine to continue to produce the fabric at the current operating speed when the yield quality of the fabric meets an expected value, or the processor adjusts the relative weights of the factors to correct the operating speed when the yield quality of the fabric does not meet the expected value.

9. The adjustment system according to claim 8, wherein the basic information of the fabric comprises at least one of a material, Danny number, fiber specification, twist, and a processing method of the fabric.

10. The adjustment system according to claim 8, wherein the step of recording and analyzing the vibration characteristics of the yarns comprises recording a motion locus of each yarn in the motion image on a projection plane perpendicular to a moving direction of the yarns, wherein the motion locus of each yarn has a plurality of position points; the processor analyzes a displacement of the position points with respect to an view point, uses the displacement as an amplitude of the motion locus, uses a time required for the position points to make one circuit of the observation point as a period of the motion locus, and constructs the factors according to the amplitude and the period of the motion locus.

11. The adjustment system according to claim 10, wherein the step of recording and analyzing the vibration characteristics of the yarns further comprises recording a motion path of the motion locus of the yarns on an axial direction of the projection plane, wherein the motion path is a projection of the position points on the axial direction, and each yarn has an initial height, the processor analyzes a maximum displacement of each height of the position points on the axial direction with respect to the initial height, and constructs the factors according to the maximum displacement.

12. The adjustment system according to claim 11, wherein the video camera is disposed in a direction parallel to the moving direction of the yarns, and a height of the video camera is aligned with the initial height of the yarns.

13. The adjustment system according to claim 8, wherein the step of adjusting the relative weights of a plurality of factors comprises determining whether one of the factors affecting the yield quality of the fabric is a positive correlation factor or a negative correlation factor, wherein the processor increases the relative weight of the positive correlation factor when the one factor is determined as a positive correlation factor or reduces the relative weight of the negative correlation factor when the one factor is determined as a negative correlation factor.

14. The adjustment system according to claim 8, wherein the yield quality of the fabric is determined according to quantity and density of defects of the yarns.

* * * * *